United States Patent [19]

Minaskanian et al.

[11] Patent Number: 4,833,150
[45] Date of Patent: May 23, 1989

[54] 1,4-DIHYDROPYRIDINES

[75] Inventors: Gevork Minaskanian, Irvine; Vithal J. Rajadhyaksha, Mission Viejo, both of Calif.

[73] Assignee: Nelson Research & Development Co., Irvine, Calif.

[21] Appl. No.: 2,008

[22] Filed: Jan. 12, 1987

Related U.S. Application Data

[63] Continuation of Ser. No. 711,815, Mar. 14, 1985, Pat. No. 4,652,573.

[51] Int. Cl.$^4$ .................. A61K 31/44; C07D 401/04
[52] U.S. Cl. .................................. 514/314; 546/167
[58] Field of Search ............ 546/272, 281, 187, 194, 546/270, 167; 544/121, 130, 131, 357, 364; 514/339, 228, 234, 236, 252, 253, 316, 318, 338, 343, 314

[56] References Cited

U.S. PATENT DOCUMENTS

| | | | |
|---|---|---|---|
| 3,325,505 | 6/1967 | Loev | 546/321 |
| 3,455,945 | 7/1969 | Loev | 546/321 |
| 3,470,297 | 9/1969 | Bossert et al. | 546/321 |
| 3,485,847 | 12/1969 | Bossert et al. | 546/321 |
| 3,511,837 | 5/1970 | Bossert et al. | 546/321 |
| 3,905,970 | 9/1975 | Bossert et al. | 546/321 |
| 3,985,758 | 10/1976 | Murakami et al. | 546/321 |
| 4,177,278 | 12/1979 | Bossert et al. | 546/257 |

(List continued on next page.)

FOREIGN PATENT DOCUMENTS 0151006 7/1985 European Pat. Off. .

OTHER PUBLICATIONS

Ferry, et al., "Photoaffinity Labelling of CA$^{2+}$ Channels with [$^3$H]azidopine," FEBS 1365 169(1), 112-118 (1984).

(List continued on next page.)

Primary Examiner—Jane T. Fan
Attorney, Agent, or Firm—Robert J. Baran; June M. Bostich

[57] ABSTRACT

Compounds having calcium channel antagonist activity of the formula:

$$R_3-O-\overset{O}{\underset{\|}{C}}-\overset{H}{\underset{}{\overset{|}{C}}}\overset{R_6}{\underset{}{}}-\overset{O}{\underset{\|}{C}}-O-A-R_4$$

with $R_2$ and $R_1$ on the pyridine ring (N–H)

wherein $R_1$ and $R_2$ are each independently amino, trifluoromethyl, pentafluoroethyl, alkoxy, lower alkenyl, or lower alkynyl or branched or unbranched lower alkyl, which is unsubstituted or is substituted with cyano, hydroxy, acyloxy, hydrazino, lower alkyl amino, or di(lower alkyl)-amino or 5 or 6 membered saturated nitrogen-containing heterocyclic-1-yl, which is unsubstituted or is substituted with oxo, hydroxy, alkyl, and hydroxy (lower alkyl) $R_3$ is straight- or branched-chain $C_1$ to $C_{12}$ alkyl, alkenyl, alkynyl, or cycloalkyl, and is either unsubstituted or substituted with hydroxy, acyloxy, cyano, di(lower alkyl) amino 5- or 6-membered saturated nitrogen-containing heterocyclic -1-yl or $R_3$ is —A—$R_4$, A is a straight- or branched-chain hydrocarbon moiety containing from 2 to 12 carbon atoms and from 0 to 2 double bonds, $R_4$ is selected from the group consisting of:

(phthalimido group), (isoindolinone group), (isoindoline with $R_5$), (succinimido), (2-pyrrolidinone), (pyrrolyl) and (dimethylpyrrolyl with CH$_3$ groups)

$R_5$ is hydrogen, nitro, cyano, azido, amino, trifluoromethyl, alkylamino, dialkylamino, halo, carboxyl, carbalkoxy, alkyl, alkenyl, alkynyl, cycloalkyl, acylamino, carboxamido, sulfonamido, and SO$_m$-(lower)alkyl where m is 0, 1, or 2 and $R_6$ is aryl or heteroaryl or a pharmaceutically-acceptable salt thereof are disclosed. Also disclosed is a method of treating hypertension and other disorders by administering an effective amount of a compound of the present invention.

17 Claims, No Drawings

U.S. PATENT DOCUMENTS

| | | | |
|---|---|---|---|
| 4,188,395 | 2/1980 | Bossert et al. | 546/257 |
| 4,258,042 | 3/1981 | Loev et al. | 544/131 |
| 4,307,103 | 12/1981 | Sato et al. | 546/272 |
| 4,348,395 | 9/1982 | Franckowiak et al. | 544/238 |
| 4,360,520 | 11/1982 | Meyer et al. | 544/224 |
| 4,393,070 | 6/1983 | Sato et al. | 546/286 |
| 4,446,325 | 5/1984 | Ohno et al. | 546/283 |
| 4,448,964 | 5/1984 | Muto et al. | 546/194 |
| 4,450,160 | 5/1984 | Temple et al. | 544/350 |
| 4,478,834 | 10/1984 | Shroff et al. | 544/126 |
| 4,483,985 | 11/1984 | Wehinter et al. | 544/131 |
| 4,485,239 | 11/1984 | Biseniex et al. | 546/321 |
| 4,487,932 | 12/1984 | Biseniex et al. | 546/321 |
| 4,491,581 | 1/1985 | Vogel | 544/238 |
| 4,491,582 | 1/1985 | Loev et al. | 544/295 |
| 4,492,703 | 1/1985 | Goldmann et al. | 424/268 |
| 4,495,192 | 1/1985 | Muto et al. | 514/318 |
| 4,495,356 | 1/1985 | Inoue et al. | 546/268 |
| 4,497,808 | 2/1985 | Zimmermann et al. | 514/222 |
| 4,500,527 | 2/1985 | Loev et al. | 514/223 |
| 4,500,528 | 2/1985 | Loev et al. | 514/228 |
| 4,500,532 | 2/1985 | Loev et al. | 514/256 |
| 4,503,223 | 3/1985 | Reilly, Jr. | 544/122 |
| 4,505,920 | 3/1985 | Loev et al. | 514/341 |
| 4,508,719 | 4/1985 | Tricerri et al. | 514/236 |
| 4,520,131 | 5/1985 | Loev et al. | 514/156 |
| 4,532,248 | 7/1985 | Franckowiak et al. | 514/358 |
| 4,568,677 | 2/1986 | Alker et al. | 514/272 |
| 4,622,332 | 11/1986 | Wehinger et al. | 514/356 |
| 4,652,573 | 3/1987 | Minaskanian et al. | 514/339 |
| 4,732,985 | 3/1988 | Alker et al. | 546/283 |

OTHER PUBLICATIONS

Thayer, et al., "An Antibody to Dihydropyridine Calcium Entry Blockers," *Biochemical Pharmacology* 35(24), 4479–4485 (1986).

Wolfe, et al., "Five-Membered Ring, II. Inter and Intramolecular Reactions of Simple Amines with N-Substituted Phthalimides. Methylamine as a Reagent for Removal of Phthaloyl Group from Nitrogen,"*Can J Chem* 48, 3372–3379 (1970).

Hogestatt, et al., "Effects of Nifedipine on Potassium-Induced Contraction and Noradrenaline Release in Cerebral and Extracranial Arteries from Rabbit," *Acta Physiol Scand* 114:283–296 (1982).

1,4-DIHYDROPYRIDINES

This is a continuation of application Ser. No. 711,815, filed Mar. 14, 1985, now U.S. Pat. No. 4,652,573, issued Mar. 24, 1987.

BACKGROUND OF THE INVENTION

This invention is concerned with certain 1,4-dihydropyridines, their preparation, pharmaceutical compositions containing them and their use as therapeutic agents, particularly as anti-ischaemic and anti-hypertensive agents.

The compounds of the invention delay or prevent the cardiac contracture which is believed to be caused by an accumulation of intracellular calcium under ischaemic conditions. Calcium overload, during ischaemia, can have a number of additional adverse effects which would further compromise the ischaemic myocardium. These include less efficient use of oxygen for ATP production, activation of mitochondrial fatty acid oxidation, and possibly, promotion of cell necrosis. Thus, the compounds are useful in the treatment or prevention of cardiac conditions, such as angina pectoris, cardiac arrythmias, heart attacks and cardiac hypertrophy. The compounds also possess vasodilator activity and are thus useful as antihypertensives and for the treatment of coronary vasospasm.

The compounds of the invention are calcium channel antagonists which are characterized by the presence of certain nitrogen-containing heterocyclic substituents in carboxylic ester groups substituted on the 3 and, optionally, also on the 5 positions of the dihydropyridine ring.

The structure and presumed mode of action of the 1,4-dihydropyridine calcium antagonists have been reviewed recently in the literature, see Meyer, et al., Annual Reports in Medicinal Chemistry, 1983, Chapter 9 and Janis, et al., J. Med. Chem 26, 775 (1983). One of the earliest compounds discovered, and still a standard against which new compounds are measured, is nifedipine (U.S. Pat. No. 3,485,847 to Bossert), in which the 2 and 6 positions are substituted by methyl groups, the 4 position by 2-nitrophenyl and the 3 and 5 positions by carboxylic acid methyl ester groups. Similar compounds are disclosed in U.S. Pat. Nos. 3,455,945; 3,325,505; and 3,441,468 to Loew and Nos. 3,470,297 and 3,511,837 to Bossert, which introduced variations in the 4-substituent. U.S. Pat. Nos. 3,905,970 to Bossert, et al., and 3,985,758 to Marakami, et al., introduced certain mono- or dialkylamino-alkylene and nitrogen-containing heterocyclic alkylene groups into one or both of the 3,5 ester groups. U.S. Pat. Nos. 4,307,103 and 4,393,070 to Sato disclose 1,4-dihydropyridines in which the 2 position is not substituted by alkyl, but instead is substituted with cyano, formyl or certain other substituents and the ester group in the 3 position may contain various substituted alkyl groups including substituted alkyl aminoalkyl, heterocyclic aminoalkyl and aroylaminoalkyl, including phthalimidoethyl. U.S. Pat. No. 4,448,964 to Muto, et al., discloses compounds in which the 3-position ester group contains certain substituted piperidinyl alkylene groups.

It is recognized that useful 1,4-dihydropyridines have a wide variety of structures; however, the need for superior activity and specificity remains, and the effect of any particular structural modification on the properties of the compound is generally unpredictable. This is particularly true of modifications in the esters at the 3 and 5 positions, and of modifications at the 2 and 5 positions.

SUMMARY OF THE INVENTION

According to the invention, there are provided novel compounds of the formula:

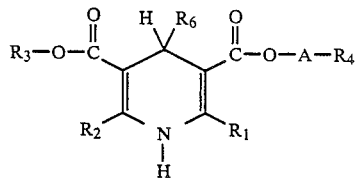

wherein $R_1$ and $R_2$ are each independently amino, trifluoromethyl, pentafluoroethyl, alkoxy, lower alkenyl, lower alkynyl, straight- or branched-chain lower alkyl which may be substituted with cyano, hydroxy, acyloxy, hydrazino, lower alkylamino, di(lower alkyl) amino, or a 5- or 6-membered saturated nitrogen containing heterocyclic-1-yl, which may in turn be substituted with oxo, hydroxy, lower alkyl and hydroxy(lower alkyl) substituents;

$R_3$ is straight- or branched-chain $C_1$-$C_{12}$ alkyl, alkenyl, alkynyl or cycloalkyl optionally containing hydroxy, alkoxy, acyloxy, cyano, di(lower alkyl)amino, 5- or 6-membered saturated nitrogen-containing heterocyclic-1-yl or —A—$R_4$, wherein A and $R_4$ are as defined below;

A is selected from the group consisting of straight-chain, branched-chain, and cyclic hydrocarbon structures containing 2 to 12 carbon atoms with from zero to two double bonds;

$R_4$ is selected from the group consisting of:

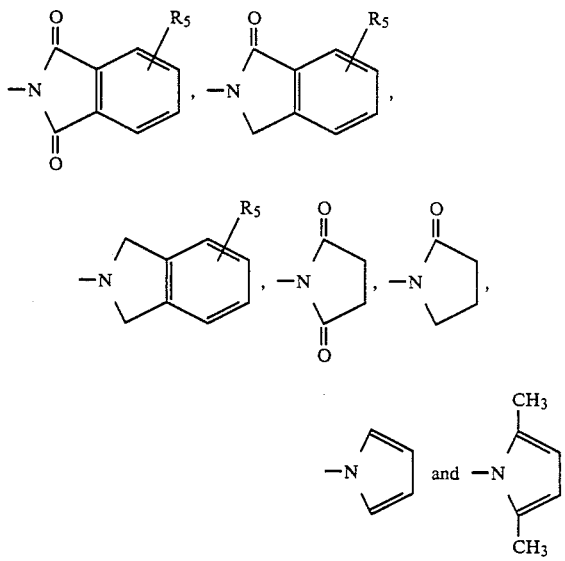

$R_5$ is hydrogen, nitro, cyano, azido, amino, trifluoromethyl, (lower alkyl)amino, di(lower alkyl)amino, halo, carboxyl, carb-lower alkoxy, lower alkyl, lower alkenyl, lower alkynyl, cyclo(lower)alkyl, (lower acyl)amino, carboxamido, sulphonamido, and $SO_m$-(lower alkyl) (m=0 to 2); and $R_6$ is aryl or hetero-aryl, and is phenyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl or benzimidazolyl, the aryl and the hetero-aryl optionally containing from 1 to 3 identical or different substituents each of which is lower alkyl, lower alkenyl, lower alkynyl, lower alkoxy, lower alkenoxy, lower alkynoxy, dioxy(lower)-alkylene, halogen, trifluoromethyl, hydroxyl, amino, (lower alkyl)amino, di(lower alkyl)amino, nitro, cyano, azido, carboxy, carb(lower)alkoxy, carboxamido, sulphonamido, or $SO_m$-(lower alkyl) or (m=0 to 2), the lower alkyl and lower alkoxy substituents in turn being optionally substituted by lower alkoxy, halogen, carboxyl, carb(lower) alkoxy, amino, lower alkylamino or di(-lower alkyl)amino;

or a pharmaceutically acceptable salt thereof.

These compounds are useful in the treatment of coronary insufficiency, angina pectoris and hypertension.

The invention also provides pharmaceutical compositions containing the above novel compounds and a pharmaceutically acceptable carrier. Preferably these compositions are in dosage form comprising a clinically effective amount of the active compound.

The invention further provides a method of antagonizing the utilization of calcium in the body of a human being or animal and of treating the above disorders.

In another embodiment of the invention there is provided a method for preparing the novel compounds.

DETAILED DESCRIPTION OF THE INVENTION

As used herein, the term "lower" when used to modify alkyl, alkoxy, alkenyl, alkynyl, and acyl shall mean "containing not more than about 6 carbon atoms." The preferred lower alkyls, alkoxys, alkenyls, alkynyls, and acyls contain not more than 4 carbon atoms.

It is particularly desirable that $R_1$ and $R_2$ be methyl. Other preferred $R_1$ and $R_2$ substituents are ethyl, n-propyl, isopropyl, n-butyl, isobutyl, t-butyl, allyl, propargyl, amino, trifluoromethyl, (lower alkyl)amino(lower alkyl), especially diethylaminoethyl and cyanomethyl.

In one preferred embodiment, $R_1$ and $R_2$ are both methyl. In another preferred embodiment, $R_1$ is methyl or ethyl and $R_2$ is not lower alkyl. In another preferred embodiment, $R_1$ is trifluoromethyl. In another, $R_2$ is trifluoromethyl. In yet another, both $R_1$ and $R_2$ are trifluoromethyl.

The term "5- or 6-membered saturated nitrogen-containing heterocyclic-1-yl" for $R_1$, $R_2$, and $R_3$ shall mean a heterocyclic moiety linked to the lower alkyl group through the heterocyclic nitrogen atom, whether or not the nitrogen atom is assigned the number "1". Suitable heterocyclic moieties include pyrrolidinyl, piperazinyl, piperidinyl, 1-methyl-4-piperazinyl, morpholinyl, etc.

"Lower alkylamino" for $R_1$ and $R_2$ includes methylamino, ethylamino, 1-propylamino, 2-propylamino, 1-butylamino, 2-butylamino, etc.

"Di-(lower alkyl)-amino" for $R_1$, $R_2$, and $R_3$ includes, for example, dimethylamino, N-methyl-N-ethylamino, N,N-diethylamino, N,N-di-(n-propyl)amino, N-methyl-N-propylamino, etc.

Examples of $R_3$ substituents include methyl, ethyl, propyl, butyl, pentyl, hexyl, heptyl, octyl, nonyl, decyl, undecyl, dodecyl, 2-hydroxyethyl, 3-hydroxy-butyl, 3-hexenyl, 1,3-butadienyl, acetylenyl, allyl, ethynyl, vinyl, isopropenyl, 2-nonyl-2-butenyl, and cyanomethyl.

Preferred $R_3$ moieties are —A—$R_4$ and lower alkyl groups (having one to six carbon atoms). Particularly preferred are methyl, ethyl, and isopropyl.

A is preferably a $C_2$ to $C_6$ alkylene group, namely ethylene, propylene, butylene, pentylene, and hexylene. Preferred $R_5$ substituents are hydrogen, carboxyl, carboxamido, carb(lower) alkoxy, and lower alkyl, particularly methyl and ethyl.

Particularly preferred $R_6$ moieties are o and m (positions 2, 3, 5, and 6) substituted and disubstituted phenyl, substituted with nitro, trifluoromethyl, cyano, azido, carboxy, carb(lower)-alkoxy, carboxamido, sulfonamido, and $SO_m$-(lower alkyl) where m is 0–2. Most preferred substituents are nitro in particular, as well as trifluoromethyl, cyano, carboxamido, and sulfonamido. Other preferred $R_6$ groups are pyridyl, furyl, and thienyl, substituted as above.

It will be appreciated that certain compounds of the invention are chiral due to their different ester functions. Accordingly, the invention embraces the pure enantiomers as well as mixtures thereof.

PHARMACEUTICAL FORMULATION

Pharmaceutically acceptable salts of the compounds of the general Formula I are prepared in the conventional manner. Acid addition salts are derived from a therapeutically acceptable acid such as hydrochloric acid, hydrobromic acid, acetic acid, propionic acid and, more preferably, from a di- or poly-basic acid such as phosphoric acid, succinic acid, fumaric acid, citric acid, glutaric acid, citraconic acid, glutaconic acid, tartaric acid, maleic acid or ascorbic acid.

A preferred embodiment of this invention is a method of treatment which comprises administering a therapeutically effective amount of a compound of the above Formula I. In general the daily dose can be from 0.01 mg/kg to 10 mg/kg per day and preferably from 0.2 mg/kg to 4 mg/kg per day, bearing in mind, of course, that in selecting the appropriate dosage in any specific case, consideration must be given to the patient's weight, general health, metabolism, age and other factors which influence response to the drug. The parenteral dosage will be approximately an order of magnitude lower than the oral dosage. Because the activities of the compounds vary somewhat, the effective dosages will also vary. The pharmacological data supplied herewith compare the compounds of the present invention to the known compounds nifedipine and nicardipine, for which clinical dosages have been established. Appropriate dosage levels for each compound can be inferred from these data.

In another embodiment of this invention there are provided pharmaceutical compositions in dosage unit form which comprise from about 1 mg to about 150 mg of a compound of the above formula I, and preferably from about 5 mg to about 100 mg.

The pharmaceutical composition may be in any form suitable for oral use, such as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents elected from the group consisting of sweetening agents, flavoring agents, coloring agents, and preserving agents in order to provide a pharmaceutically elegant and palatable preparation. Tablets may contain the active ingredient in admixture with non-toxic pharmaceutically acceptable excipients which are suitable for manufacture of tablets. These excipients may be inert diluents, for example calcium carbonate, sodium carbonate, lactose, calcium phosphate; granulating and disintegrating agents, such as corn starch, gelatine or acacia; and lubricating agents, such as magnesium stearate, stearic acid or talc. The tablets may be uncoated or they may be coated by known techniques to delay disintegration and absorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate or kaoline, or as soft gelative capsules wherein the active ingredient is mixed with an oil medium, for example, arachis oil, liquid paraffin or olive oil.

The present invention also embraces aqueous suspensions containing the active compoud in admixture with suitable pharmacologically-accepted excipients. Such excipients include suspending agents, for example sodium carboxymethylcellulose, methycellulose, hydroxypropylmethylcellulose, sodium alginate, polyvinylpyrrolidone, gum tragacanth and gum acacia; dispersing or wetting agents such as a naturally-occurring phosphatide, for example lecithin, or a condensation products of an alkylene oxide with fatty acids, for example polyoxyethylene stearate, or condensation prodcts of ethylene oxide with long chain aliphatic alcohols, for example heptadecaethyleneoxycetanol, or condensation products of ethylene oxide with partial esters derived from fatty acids and a hexitol, for example polyoxyethylene sorbitol monooleate, or condensation product of ethylene oxide with partial esters derived from fatty acids and hexitol anhydrides, for example polyoxyethylene sorbitan monooleate. The said aqueous suspensions may also contain one or more preservatives, for example ethyl, or n-propyl-p-hydroxy benzoate, one or more coloring agents, one or more flavoring agents, and one or more sweetening agents, such as sucrose, saccharin, aspartame, mannitol, sorbitol, or sodium or calcium cyclamate.

Dispersable powders and granules suitable for preparation of an aqueous suspension by the addition of water provide the active ingredient in admixture with a dispersing or wetting agent, suspending agent, and one or more preservatives. Suitable dispersing or wetting agents and suspending agents are exemplified by those already mentioned above. Additional excipients, for example, sweetening, flavoring, and coloring agents, may also be present.

Syrups and elixirs may be formulated with sweetening agents, for example glycerol, sorbitol or sucrose. Such formulations may also contain a demulcent, a preservative, and flavoring and coloring agents.

The pharmaceutical compositions may also be in the form of a sterile injectable preparation, for example as a sterile injectable aqueous suspension. This suspension may be formulated in a conventional manner using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol.

The pharmaceutical compositions may be tableted or otherwise formulated so that for every 100 parts by weight of the composition there are present between 5 and 95 parts by weight of the active ingredient and preferably between 25 and 85 parts by weight of the active ingredient. The dosage unit form for humans will generally contain between about 1 mg and 100 mg of the active ingredient of the Formula I set forth above.

From the foregoing formulation discussion it should be apparent that the compositions of this invention can be administered orally or parenterally. The term parenteral as used herein includes subcutaneous injection, intravenous, intramuscular, or intrasternal injection or infusion techniques.

The compounds of the present invention may also be administered transdermally with the use of an appropriate transdermal vehicle. The preferred vehicle is 1-dodecylazacycloheptan-2-one, disclosed in U.S. Pat. No. 4,405,616.

This invention also incudes a method for treating coronary insufficiency (poor circulation, due to cardiac hypertrophy or to other causes), hypertension, angina pectoris, cardiac arrythmia, heart attack, or coronary vasospasm by administering an effective amount of a compound of the present invention. The invention also compounds a method for effecting calcium channel antagonist activity in a mammal, such as a human, by administering an effective amount of a compound of Formula I.

The compounds of Formula I, above, may be prepared by the following general syntheses:

Process 1 according to the procedure described by Fox, et al., in J. Org. Chem. 16, 1259 (1951):

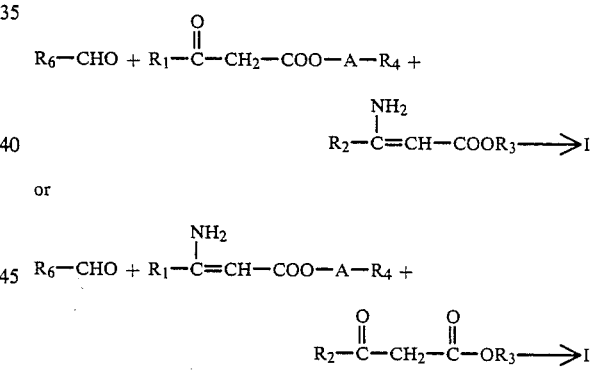

wherein $R_1$, $R_2$, $R_3$, $R_4$, A, and $R_6$ have the same meaning as defined above.

The details of Process No. 1 are as follows:

The molar ratio of the starting materials in the reaction mixture is in the range of from about 1.0:0.8:0.8 to 1.0:4.0:4.0 respectively and preferably from about 1.0:0.9:0.9 to 1.0:1.5:1.5.

The reaction is carried out in the presence or absence of an alcohol such as methanol, ethanol, isopropanol, etc., a halogenated hydrocarbon such as chloroform, carbon tetrachloride, etc., an aromatic hydrocarbon such as benzene, toluene, etc., an ether such as tetrahydrofuran, dioxane, etc., and an aprotic polar solvent such as acetonitrile, dimethyl formamide, water or the like, between room temperature and 150° C., preferably 30° to 100° C. Separation of the desired product from the reaction mixture is effected by conventional operations such as concentration, extraction, recrystallization, and flash chromatography.

Substituted β-ketoesters were prepared by transesterification, thus:

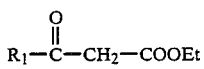

(1–1.5 mol) is treated with $R_4$—A—OH (1 mol) and

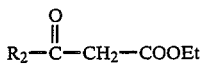

(1–1.5 mol) is treated with $R_3$—OH (1 mol) in a reaction vessel at 140°–150° C. for 6–12 hours in the presence of small amounts of Na. Ethanol formed is preferably removed by a flow of inert gas through the reaction vessel, thereby forcing the reaction to completion. From the residue, the product is isolated by distillation, flash chromotography or crystallization.

Substituted β-ketoesters, where in $R_1$ and $R_2$ are specifically —$CH_3$, for example:

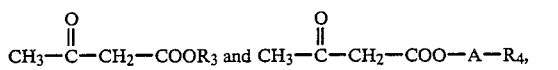

wherein $R_3$ and $R_4$ have the meaning defined above, are prepared by reacting alcohols of the formula $R_3OH$ and $R_4$—A—OH respectively, with a source of ketene, for example diketene, or diketene-acetone adduct in refluxing toluene. A catalytic amount of p-toluenesulfonic acid is used in the alcohol and diketene-acetone adduct reaction and acetone is removed on concentration. The product is purified by distillation, crystallization or flash chromatography.

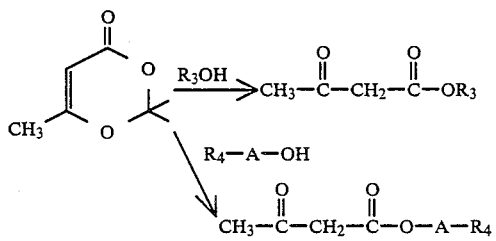

Substituted β-aminoacrylates, represented by the formulas

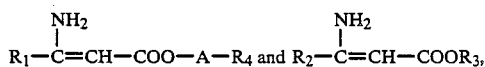

may be prepared by bubbling ammonia gas into a solution of a β-ketoester in alcohol, preferably methanol or ethanol, at from 5°–25° C. for 5 to 15 hours. The product is isolated by filtration, by distillation under vacuum or by flash chromatography.

The β-aminoacrylates may be also prepared by mixing, for example, 0.5 mole of ethyl or methylacetoacetate in 200 ml of methanol and 100 ml of saturated sodium acetate and passing through the appropriate nitrile ($R_3CN$ or $R_4CN$) for several hours. The reaction mixture is poured into ice water and the organic layer is extracted with ether. The ether solution is dried and concentrated and the residue is distilled. A mixture of about 0.1 mole of said residue and 50 ml of 30% ammonium hydroxide or sodium hydroxide is stirred for a long period. The reaction mixture is extracted with methylene chloride and the methylene chloride extracts are dried and concentrated. Fractional distillation of the residue results in the substituted β-aminoacrylate.

Further, Process Nos. 2–6 are illustrated by the following reaction schemes:

Process 2 according to the procedure described by Loev, et al., J. Med. Chem, 17, 956 (1974):

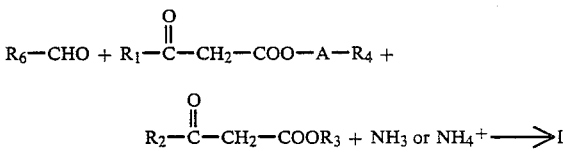

Process 3 according to the procedure described by Iwanami, et al., Chem. Pharm. Bull. 27, 1426 (1979):

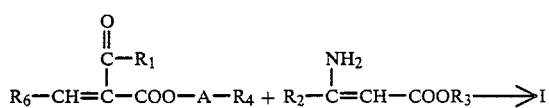

Process 4 according to the procedure described by Iwanami, et. al., Chem. Pharm. Bull. 27, 1426 (1979)

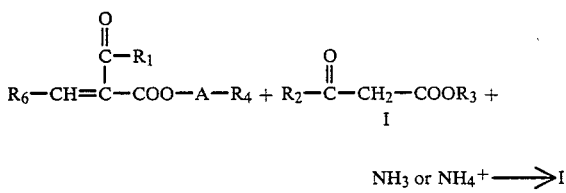

Process 5 according to the procedure described by Shibanuma, et. al., Chem. Pharm. Bull. 28, 2809 (1980)

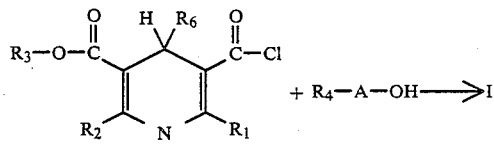

Process 6 according to the procedure described by Loev, et. al., U.S. Pat. No. 3,511,847 (1970)

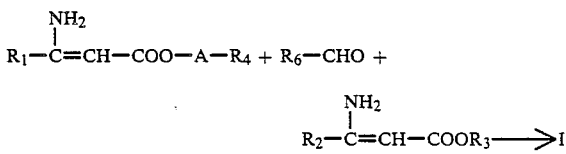

The following examples illustrate some preferred embodiments of the present invention.

EXAMPLE 1

2,6-dimethyl-3-(2-phthalimidocarbethoxy)-4-(3-methylphenyl)-5-carbmethoxy-1,4-dihydropyridine A. 2-hydroxyethyl phthalimide A suspension of 71.8 g (0.48 mol) of phthalic anhydride in 30.5 g (0.50 mo.) of 2-aminoethanol was swirled resulting in a vigorous exothermic reaction. The swirling was continued until no solid remained. The mixture was located in an oil bath at 100° C. for 30 minutes and, after cooling to room temperature, 200 ml of hot water was added. The product precipitated as a white solid, which was filtered and dried. Yield 56 g (61%); m.p. 120°–125° C. NMR: (CDCl$_3$) δ 3.7 (4H,S), 3.9 (1H,S), 7.5 (4H, m).

B. 2-phthalimidoethyl acetoacetate

Procedure 1: A mixture of 60 g (0.31 mol) of 2-hydroxyethyl phthalimide and 45 g (0.35 mol) of ethyl acetoacetate was heated in an oil bath at 145° C. for 48 hours. Ethanol was removed with nitrogen flow through the flask during the course of the reaction and the residual ethanol was removed under high vacuum. The remaining solid was recrystallized from acetone/diethyl ether/petroleum ether. Yield 40 g (46%); m.p. 87°–90° C.; NMR: (CDCl$_3$) δ 2.2 (3H,S), 3.4 (2H,S), 3.8 (2H,m), 4.3 (2H,m), 7.7 (4H,m).

Procedure 2: A solution of 36.67 (0.192 mol) of 2-hydroxyethyl phthalimide, 29.99 g (0.211 mol) of 2,2,6-trimethyl-1,3-dioxen-4-one, and 0.2 g of p-toluenesulfonic acid in 200 ml of toluene was refluxed for 12 hours under nitrogen. The mixture was cooled to room temperature and washed with 10% sodium bicarbonate and brine. The organic phase was separated, dried over MgSO$_4$, and concentrated in vacuo to give a crude oil which was subjected to flash chromatography (silica gel, 7:3 petroleum ether/ethyl acetate). The isolated solid was recrystallized from petroleum ether/ethyl acetate to yield 31.61 g (59.8%) of a white solid with m.p. and NMR data identical to the material prepared by Procedure 1.

C. 2,6-dimethyl-3-(2-phthalimidocarbethoxy)-4-(3-methylphenyl)-5-carbmethoxy-1,4-dihydropyridine A solution of 7.0 g (0.25 mol) of 2-phthalimidoethyl acetoacetate and 3.1 g (0.025 mol) of methyl3-aminocrotonate in 150 ml of 2-propanol was refluxed for 15 hours under nitrogen. The solvent was removed in vacuo and the residue was subjected to flash chromatography (silica gel, 1:1 petroleum ether/ethyl acetate). The isolated product was recrystallized in dichloromethane/hexane to give 3.5 g (50%) of a pale yellow solid; m.p. 188°–190° C. NMR: (CDCl$_3$) δ 2.1 (9H,d), 3.5 (3M,s), 3.7 (2H,m), 4.2 (2H,m), 4.6 (1H,s), 5.8 (1H,s), 7.2 (8H,m).

EXAMPLE 2

2,6-dimethyl-3-(2-phthalimidocarbethoxy)-4-(3-nitrophenyl)-5-carbmethoxy-1,4-dihydropyridine A solution of 3.02 g (0.02 mol) of 3-nitrobenzaldehyde, 2.36 g (0.02 mol) of methyl-3-aminocrotonate, and 5.72 g (0.02 mol) of 2-phthalimidoethyl acetoacetate in 150 ml of 2-propanol was refluxed for 15 hours under nitrogen. The solvent was removed in vacuo, and the residue was subjected to flash chromatography (silica gel, 1:1 dichloromethane/hexane). The product was isolated and recrystallized from 1:1 dichloromethane/hexane to yield 3.0 g (30%) of a pale yellow solid; m.p. 181.5°–182.5° C. NMR: (CDCl$_3$); δ 2.3 (6H,s), 3.5 (3H,s), 3.9 (2H,m), 4.2 (2H,m), 4.9 (1H,s), 6.0 (1H,s), 7.0–8.0 (8H,m).

EXAMPLE 3

2-6-dimethyl-3-(2-phthalimidocarbethoxy)-4-(3-trifluoromethylphenyl)-5-carbomethoxy-1,4-dihydropyridine A solution of 627 mg (3.6 m mol) of 3-trifluoromethyl benzaldehyde, 1.0 g (3.6 m mol) of 2-phthalimidoethyl acetoacetate, and 419 mg (3.6 m mol) of methyl 3-aminocrotonate in 50 ml of 2-propanol was refluxed for 15 hours under nitrogen. After removal of solvent in vacuo, the product was purified via preparative thin layer chromatography (silica gel, 1:1 ethyl acetate/petroleum ether) to yield 130 mg of a hygroscopic yellow solid. NMR: (CDCl$_3$) δ 2.2 (6H,t), 3.8 (5H,m), 4.2 (2H,m), 4.8 (1M,s), 6.5 (1H,s), 7.4 (8H,m).

EXAMPLE 4

2,6-dimethyl-3,5-di(2-phthalimidocarbethoxy)-4-(3-nitrophenyl)-1,4-dihydropyridine A solution of 137 mg (0.9 m mol) of 3-nitrobenzaldehyde, 0.5 g (1.82 m mol) of 2-phthalimidoethyl acetoacetate, and 0.16 ml (2.4 m mol) of 14.7M ammonium hydroxide in 40 ml of 2-propanol was refluxed for 15 hours under nitrogen. The solvent was removed in vacuo and the residue was subjected to flash chromatography (silica gel, 3:1 petroleum ether/ethyl acetate) to yield 50 mg of pale yellow product; m.p. 92°–94° C.; NMR: (CDCl$_3$) δ 2.2 (6M,s), 3.8 (4H,m), 4.2 (4H,m), 4.8 (1H,s), 6.1 (1H,s), 7.2 (12H,m).

EXAMPLE 5

2,6-dimethyl-3-(3-phthalimidocarbopropoxy-4-(3-nitrophenyl)-5-carbomethoxy-1,4-dihydropyridine A. N-(3-hydroxypropyl)phthalimide A solution of 18.95 g (0.25 mo.) of 3-aminopropanol and 37.0 g (0.25 mol) of phthalic anhydride in 25 ml of dry toluene was refluxed for three hours using a Dean-Stark apparatus. The mixture was cooled, concentrated in vacuo, dissolved in dichloromethane and washed with water. The evaporated organic phase was dried over magnesium sulfate, concentrated in vacuo, and distilled at 183°–184° C. (0.1 mm Hg) to give 28.18 g (55%) of a white solid; m.p. 75°–77° C.; NMR: (CDCl$_3$) δ 1.9 (2H,q), 3.65 (5H,m), 7.6 (4H,s).

B. 3-phthalimidopropyl acetoacetate

A solution of 22.8 g (0.111 mol) of N-3-hydroxypropyl phthalimide and 14.46 g (0.111 mol) of ethyl acetoacetate was heated at 145°–150° C. for 12 hours. Ethanol was removed with nitrogen flow during the course of the reaction. The mixture was cooled to room temperature, dissolved in dichloromethane, and washed with brine. The separated organic phase was dried over magnesium sulfate, concentrated in vacuo, and distilled at 211°–219° C. (0.125 mm Hg) to yield 17.3 g (54%) of a white solid; m.p. 67°–71° C. NMR: (CDCl$_3$) δ 2.0 (2H,m), 2.2 (3H,s), 3.3 (2H,s), 3.7 (2H,t), 4.05 (2M,t), 7.62 (4H,d).

C. 2,6-dimethyl-3-(3-phthalimidocarbopropoxy)-4-(3-nitrophenyl)-5-carbomethoxy-1,4-dihydropyridine A solution of 7.0 g (0.24 mol) of phthalimidopropyl acetoacetate, 3.65 g (0.02 mol) of 3-nitrobenzaldehyde, and 2.79 g (0.02 mol) of methyl 3-aminocrotonate in 145 ml of 2-propanol was heated at 80° C. under nitrogen for 36 hours. On cooling to room temperature a pale yellow solid precipitated which was filtered and recrystallized from dichloromethane/petroleum ether. Yield 7.56 g (60%) m.p. 169°–172° C. NMR: (CDCl$_3$) w 1.95 (2H,m), 2.35 (6H,5), 3.6 (5H,m), 4.0 (2H,t), 5.0 (1H,s), 6.0 (1H,s), 7.55 (8H,m).

EXAMPLE 6

2,6-Dimethyl-3-(6-phthalimidocarbohexoxy)-4-(3-nitrophenyl)-5-carbomethoxy-1,4-dihydropyridine A. N-(6-hydroxyhexyl)phthalimide A solution of 23.78 g (0.16 mol) of 6-aminohexanol in 190 ml of toluene was refluxed for 12 hours using a Dean-Stark apparatus. The mixture was cooled and concentrated in vacuo to a white solid. Recrystallization from dichloromethane/petroleum ether gave 28.04 g (70.42%) of product m.p. 51°–53° C. NMR: (CDCl$_3$) w 1.45 (8H, bs), 2.1 (1H, s), 3.55 (4H, m), 7.57 (4-H, m).

B. 6-phthalimidohexyl acetoacetate

A mixture of 22.1 g (0.09 mol) of N-(6-hydroxyhexyl) phthalimide and 10.2 g (0.08 mol) of ethyl acetoacetate was heated in an oil bath at 145° C. under nitrogen for 15 hours. After drying on high vacuum the residue was subjected to flash chromatography (silica gel, 7:3 petroleum ether/ether). The product was isolated as 12.9 g (75%) of a pale yellow oil b.p. 218°–226° C./0.15 mm. NMR: (CDCl$_3$) w 1.5 (8H, m), 2.21 (3H, s), 3.35 (2H, s), 3.55 (2H, m), 3.99 (2H, t), 7.5 (4H, m).

C. 2,6-Dimethyl-3-(6-phthalimidocarbohexoxy-4-(3-nitrophenyl)-5-carbomethoxy-1,4-dihydropyridine A solution of 7.0 g (0.02 mol) of N-(6-phthalimidohexyl acetoacetate), 3.2 g (0.02 mol) of 3-nitrobenzaldehyde and 2.4 g (0.02 mol) of methyl 3-aminocrotonate in 125 ml. of 2-propanol was refluxed for 24 hours under nitrogen. The solvent was removed in vacuo and the residue was subjected to flash chromatography (silica gel, 7:3 petroleum ether/ethyl acetate) to give a pale yellow solid. Recrystallization from methanol gave 4.9 g (55%) of the product m.p. 134°–140° C. NMR: CDCl$_3$) δ 1.45 (8H, bs), 2.85 (6H, s), 3.55 (5H, m), 4.3 (2H, t), 4.99 (1H, s), 6.3 (1H, s), 7.55 (8H, m).

EXAMPLE 7

2,6-Dimethyl-3-(2-phthalimidinocarbethoxy)-4-(3-nitrophenyl)-5-carbomethoxy-1,4-dihydropyridine A. N-(2hydroxyethyl)phthalimidine A mixture of 15.9 g (0.26 mol) of 2-aminoethanol and 34.8 g (0.26 mol) of phthalide was heated at 190° C. for 6 hours using a Dean-Stark trap. The resultant known solid was subjected to flash chromatography (silica gel, dichloromethane) to yield 30 g (63%) of a white solid m.p. 119°–120° C., NMR: (CDCl$_3$) δ 3.6 (4H, m), 4.3 (2H, s), 4.4 (1H,s), 7.4 (4H, m).

B. N-(2-phthalimidino)ethyl acetoacetate

A mixture of 9.7 g (55 m mol) of N-(2-hydroxyethyl) phthalimidine, 14.2 g (0.11 mol) ethyl acetoacetate and 50 mg of sodium was heated in an oil bath at 140°–150° C. for 6 hours. The residual ethanol was removed under high vacuum and the resulting oil was subjected to flash chromatography (silica gel, 1:1 dichloromethane/petroleum ether) to give 5.0 g (35%) of an orange oil. NMR: (CDCl$_3$) δ 2.1 (3H, s), 3.3 (2H, s), 3.8 (2H, m) 4.3 (4H, m), 7.3 (4H, m)

C. 2,6-Dimethyl-3-(2-phthalimidinocarbethoxy)-4-(3-nitrophenyl)-5-carbomethoxy-1,4-dihydropyridine A solution of 2.0 g (7.7 m mol) of N-(2-phthalimidino)ethyl acetoacetate, 1.16 g (7.7 m mol) of 3-nitrobenzaldehyde, and 0.89 g (7.7 m mol) of methyl 3-aminocrotonate in 50 ml of 2-propanol was heated at 80°–85° C. under nitrogen for 15 hours. The mixture was concentrated in vacuo and subjected to flash chromatography (silica gel, 1:1 petroleum ether/ethyl acetate) to yield 1.90 g of a pale yellow solid, m.p. 170°–175° C. NMR: (CDCl$_3$) δ 2.3 (6H, s), 3.5 (3H, s), 3.7 (2H, m), 4.1 (4H, m), 4.9 (1H, s), 6.8–7.9 (9H, m)

EXAMPLE 8

2,6-Dimethyl-3-(2-isoindolinylcarbethoxy)-4-(3-nitrophenyl)-5-carbomethoxy-1,4-dihydropyridine A. 2-(3-tolylsulfonyl)isoindoline A solution of 34.2 g (0.2 mol) of p-toluenesulfonamide in 100 ml of dry N,N-dimethylformamide was added dropwise to a suspension of 18.9 g (0.42 mol) of sodium hydride (50% oil dispersion) in 60 ml of N,N-dimethylformamide. The reaction was stirred at room temperature for one hour, followed by one hour at 60° C. A solution of 52.8 g (0.2 mol) of α,α'-dibromo-O-xylene in 300 ml of N,N-dimethylformamide was added at such a rate that the temperature of the reaction mixture remained between 60°–70° C. After further stirring for 48 hours at room temperature under nitrogen ice water was added to the reaction mixture. The precipitated solid was filtered and recrystallized from hot ethanol. Yield 33.58 g, m.p. 175°–177° C. NMR (CDCl$_3$) δ 2.32 (3H, s), 4.5 (4H,s), 7.25 (8H, m)

B. Isoindoline

A solution of 12.0 g (0.044 mol) of 2-(p-tolylsulfonyl) isoindoline, 12.0 g (0.13 mol) of phenol, 90 ml of 48% HBr, and 15 ml (0.201 mol) of propionic acid was refluxed for two hours. The mixture was cooled to room temperature, triturated with diethyl ether, and then added to a solution of 75 gm of sodium hydroxide in 200 ml of cold water. This mixture was extracted with diethyl ether and the combined ether extracts were washed with water. The organic phase was dried over magnesium sulfate, concentrated in vacuo and kugelrohr distilled to give 3.28 g (61%) of a white solid, m.p. 118°–127° C. NMR (CDCl$_3$) δ 2.2 (1H,s), 4.0 (4H, s), 6.95 (4H, s)

C. 2-(2-hydroxyethyl) isoindoline

A solution of 2.85 g (0.0252 mol) of isoindoline, 2.99 g (0.0252 mol) of 2-bromoethanol and 5.09 g (0.05 mol) of triethylamine in 100 ml of dry toluene was refluxed for 12 hours. After cooling the mixture was filtered, concentrated in vacuo, dissolved in ethyl acetate and washed with water. The organic phase was dried over magnesium sulfate and concentrated in vacuo to yield 2.58 g (63%) of a dark red oil. NMR (CDCl$_3$) δ 2.78 (2H, t), 3.52 (2H, t), 3.82 (4H, s), 7.0 (4H, s)

D. (2-Isoindolinyl)ethyl acetoacetate

A solution of 4.67 g (0.029 mol) of 2-(2-hydroxyethyl) isoindoline and 3.72 g (0.029 mol) of ethyl acetoacetate was heated at 100°–110° C. under nitrogen for 36 hours. Ethanol was removed with nitrogen flow during the course of the reaction. The mixture was subjected to flash chromatography (silica gel, 1:1 ethylacetate/petroleum ether) to give 1.54 g (22%) of a dark oil. NMR (CDCl$_3$) δ 2.2 (3H, s), 2.94 (2H, t), 3.4 (2H, s), 3.9 (4H, s), 4.24 (2H, t), 7.04 (4H, s)

E. 2,6-Dimethyl-3-(2-isoindolinylcarbethoxy)-4-(3-nitrophenyl)-5-carbomethoxy-1,4-dihydropyridine A solution of 1.54 g (6.2 m mol) of 2-isoindolinylethyl acetoacetate, 0.942 g (6.2 m mol) of 3-nitrobenzaldehyde and 0.717 g (6.2 m mol) of methyl 3-aminocrotonate in 37 ml of 2-propanol was heated at 80° C. under nitrogen for 48 hours. The crude mixture was concentrated in vacuo and subjected to flash chromatography (silica gel, 1:1 petroleum ether/ethyl acetate) to give 1.38 g (46%) of a brown solid, m.p. 63°–69° C. NMR (CDCl$_3$) δ 2.29 (6H, s), 2.8 (2H, t), 3.5 (2H, s), 3.8 (4H, s), 4.12 (2H, t), 5.0 (1H, s), 6.2 (1H, bs), 7.33 (8H, m).

EXAMPLE 9

2,6-Dimethyl-3-(2-succimimidocarbethoxy)-4-(3-nitrophenyl)-5-carbomethoxy-1,4-dihydropyridine A. N-(2-hydroxyethyl)succimimide 24.64 g (0.40 mol) of 2-aminoethanol was added dropwise under nitrogen to 40.0 g (0.4 mol) of succinic anhydride. After the addition, the reaction mixture was stirred for 10 minutes at room temperature, followed by 35 minutes at 105° C. The reaction mixture was cooled, triturated with diethyl ether, dried, concentrated and distilled at 183°–184° C./0.1 mm Hg to give 29.69 g (52%) of a white solid, m.p. 60°–62° C. NMR (CDCl$_3$) δ 2.65 (4H, s), 3.35 (1H, s), 3.6 (4H, s).

B. (2-succimimido)ethyl acetoacetate

A solution of 21.56 g (0.15 mol) of N-(2-hydroxyethyl) succinimide and 19.6 g (0.15 mol) of ethyl acetoacetate was heated at 145° C. under nitrogen for 12 hours. Ethanol was removed with nitrogen flow during the course of the reaction. The mixture was cooled, dissolved in dichloromethane and washed with water. The organic phase was dried over magnesium sulfate and concentrated in vacuo. Distillation of the residue (144°–155° C./0.1 mm) gave 15.72 g (46%) of a yellow oil. NMR (CDCl$_3$) δ 2.2 (3H, 2), 2.65 (4H, s), 3.32 (2H, s), 3.62 (2H, m), 4.2 (2H, m)

C. 2,6-Dimethyl-3-(2-succimimidocarbethoxy)-4-(3-nitrophenyl)-5-carbomethoxy-1,4-dihydropyridine A solution of 7.0 g (0.03 mol) of (2-succinimido)ethyl acetoacetate, 4.7 g (0.03 mol) of 3-nitrobenzaldehyde and 3.5 g (0.03 mol) of methyl 3-aminocrotonate in 100 ml of 2-propanol was refluxed under nitrogen for 15 hours. The mixture was concentrated, dried under high vacuum and then subjected to flash chromatography (silica gel, 1:1 ethyl acetate/petroleum ether) to give a pale yellow solid. Recrystallization from dichloromethane/petroleum ether yielded 4.5 g (32%) of the product, m.p. 184°–186° C. NMR (CDCl$_3$) δ 2.3 (6H, s), 2.6 (4H, s), 3.6 (5H, t), 4.1 (2H, m), 4.9 (1H, s), 6.1 (1H, s), 7.5 (4H, m)

EXAMPLE 10

2,6-Dimethyl-3-[2-(2-oxopyrrolidino)carbethoxy]-4-(3-nitrophenyl)-5-carbomethoxy-1,4-dihydropyridine A. 2-(2-oxopyrrolidino)ethyl acetoacetate A mixture of 20 g (0.16 mol) of 1-hydroxyethyl-2-oxo-pyrrolidine, 40 g (0.31 mole) of ethyl acetoacetate and 100 mg of sodium was heated at 140°–150° C. for six hours. Residual ethanol was removed in vacuo and the resultant oil was kugelrohr distilled (200° C./1 mm) to give 1.38 g (40%) of the product. NMR (CDCl$_3$) δ 2.1 (7H, m), 3.4 (6H, m) 4.1 (2H, t)

B. 2,6-Dimethyl-3-[2-(2-oxopyrrolidino)carbethoxy]-4-(3-nitrophenyl)-5-carbomethoxy-1,4-dihydropyridine A solution of 4.0 g (0.019 mol) of 2-(2-oxopyrrolidino) ethyl acetoacetate, 7.8 g (0.019 mol) of 3-nitrobenzaldehyde and 2.2 g (0.019 mol) of methyl 3-aminocrotonate in 100 ml of 2-propanol was refluxed for 15 hours under nitrogen. The solvent was removed in vacuo and the residue was subjected to flash chromatography (silica gel, 9:1 petroleum ether/ethyl acetate) to give a yellow solid. Recrystallization from ethyl acetate/diethyl ether/petroleum ether gave 4.0 g of the product, m.p. 112°–114° C. NMR (CDCl$_3$) δ 2.3 (10H, s), 3.3 (4H, m), 3.5 (3H, s), 4.0 (2H, m), 5.0 (1H, s), 7.4 (5H, m)

EXAMPLE 11

2,6-Dimethyl-3-[2-(2,5-dimethylpyrrolyl)carbethoxy]-4-(3-nitrophenyl)-5-carbomethoxy-1,4-dihydropyridine A. 1-(2-hydroxyethyl)-2,5-dimethylpyrrole A mixture of 20 g (0.33 mol) of 2-aminoethanol and 38 g (0.33 mol) of 2,5-hexanedione was stirred until the vigorous reaction subsided. 100 ml of toluene was added and the solution was refluxed to 15 hours in a Dean-Stark apparatus. The solvent was removed in vacuo and the resulting oil was kugelrohr distilled at 110° C./1.5 mm to yield 40 g (87%) of a white solid. NMR (CDCl$_3$) δ 2.1 (1H, s), 2.2 (6H, s), 3.7 (4H, m), 5.6 (2H, s)

B. 2-(2,5-dimethylpyrrolyl)ethyl acetoacetate

A mixture of 28 g (0.20 mol) of 1-(2-hydroxyethyl)-2,5-dimethylpyrrole and 31.2 g (0.24 mol) of ethyl acetoacetate was heated at 145° C. for six hours. Residual ethanol was removed in vacuo and kugelrohr distillation of the residue gave 27 g (61%) of pale green oil. NMR (CDCl$_3$) δ 2.1 (9H, s), 3.3 (2H, s), 4.0 (4H, m) 5.6 (2H, s)

C. 2,6-Dimethyl-3-[2-(2,5-dimethylpyrrolyl)carbethoxy]-4-(3-nitrophenyl)-5-carbomethoxy-1,4-dihydropyridine A solution of 2.3 g (0.02 mol) of 2-(2,5-dimethylpyrrolyl) ethyl acetoacetate, 2.3 g (0.02 mol) of methyl 3-aminocrotonate and 3.39 g (0.02 mol) of 3-nitrobenzaldehyde in 100 ml of 2-propanol was refluxed for 15 hours under nitrogen. The solvent was removed in vacuo and the resulting solid was subjected to flash chromatography (silica gel, 8:1:1 petroleum ether/dichloromethane/ethyl acetate). The product was recrystallized from petroleum ether/dichloromethane/diethylether to give 3.5 g (39%) of an air- and light-sensitive solid, m.p. 156.5°–160° C. NMR (CDCl$_3$) δ2.1 (6H, s), 2.2 (3H, s), 2.3 (3H, s), 3.5 (3H, s), 3.9 (4H, m), 5.0 (1H, s), 5.6 (2H, s), 6.1 (1H, s), 7.8 (4H, m)

EXAMPLE 12

2,6-Dimethyl-3,5-(2,5-dimethylpyrrolylcarbethoxy)-4-(3-nitrophenyl)-1,4-dihydropyridine A solution of 2.0 g (0.01 mol) of 2-(2,5-dimethylpyrrolyl) ethyl acetoacetate, 0.73 g (0.005 mol) of 3-nitrobenzaldehyde and 0.48 ml of concentrated ammonium hydroxide in 6 ml of absolute ethanol was refluxed under nitrogen for six hours and then stirred overnight at room temperature. The solvent was removed in vacuo and the resulting solid was purified by flash chromatography on silica (8:2 petroleum ether/ethyl acetate). The product was recrystallized from methylene chloride/methanol to give 0.62 g of a deep yellow powder, m.p. 167°–170° C. NMR (CDCl$_3$) δ: 2.1 (12H, s) 2.23 (6H, s), 3.91 (8H, m), 4.9 (1H, s), 5.58 (5H, s), 7.1 (2H, m) and 7.8 (2H, m)

EXAMPLE 13

The general procedure of Example 2 is repeated, except that the 3-nitrobenzaldehyde utilized therein is replaced in successive runs by an equimolar amount of
(a) 2-nitrobenzaldehyde,
(b) 2-chlorobenzaldehyde, (c) 3-chlorobenzaldehyde
(d) 3-cyanobenzaldehyde,
(e) 3-methoxybenzaldehyde,
(f) 2-bromobenzaldehyde,
(g) 2-chloro-6-fluorobenzaldehyde,
(h) 2-chloro-5-nitrobenzaldehyde,
(i) 3-bromobenzaldehyde,
(j) 2,6-dinitrobenzaldehyde,
(k) 2-chloro-6-nitrobenzaldehyde,
(l) 2-fluorobenzaldehyde,
(m) 3-fluorobenzaldehyde,
(n) 2-nitro-5-chlorobenzaldehyde,
(o) 5-bromo-2-furaldehyde,
(p) 2-furaldehyde,
(q) indole-3-carboxaldehyde,
(r) 5-nitro-2-furaldehyde,
(s) 2-pyridinecarboxaldehyde,
(t) 3-pyridinecarboxaldehyde,
(u) 2-thiophenecarboxaldehyde,
(v) 3-thiophenecarboxaldehyde
(w) 3-quinolinecarboxaldehyde,
(x) pyrrole-2-carboxaldehyde, and
(y) 1-methylpyrrole-2-carboxaldehyde,
to produce respectively,
(a) 2,6-Dimethyl-3-(2-phthalimidocarbethoxy)-4-(2-nitrophenyl)-5-carbomethoxy-1,4-dihydropyridine,
(b) 2,6-Dimethyl-3-(2-phthalimidocarbethoxy)-4-(2-chlorophenyl)-5-carbomethoxy-1,4-dihydropyridine,
(c) 2,6-Dimethyl-3-(2-phthalimidocarbethoxy)-4-(3-chlorophenyl)-5-carbomethoxy-1,4-dihydropyridine,
(d) 2,6-Dimethyl-3-(2-phthalimidocarbethoxy)-4-(3-cyanophenyl)-5-carbomethoxy-1,4-dihydropyridine,
(e) 2,6-Dimethyl-3-(2-phthalimidocarbethoxy)-4-(3-methoxy-phenyl)-5-carbomethoxy-1,4-dihydropyridine,
(f) 2,6-Dimethyl-3-(2-phthalimidocarbethoxy)-4-(2-bromophenyl)-5-carbomethoxy-1,4-dihydropyridine,
(g) 2,6-Dimethyl-3-(2-phthalimidocarbethoxy)-4-(2-chloro-6-fluorophenyl)-5-carbomethoxy-1,4-dihydropyridine,
(h) 2,6-Dimethyl-3-(2-phthalimidocarbethoxy)-4-(2-chloro-5-nitrophenyl)-5-carbomethoxy-1,4-dihydropyridine,
(i) 2,6-Dimethyl-3-(2-phthalimidocarbethoxy)-4-(3-bromophenyl)-5-carbomethoxy-1,4-dihydropyridine,
(j) 2,6-Dimethyl-3-(2-phthalimidocarbethoxy)-4-(2,6-dinitrophenyl)-5-carbomethoxy-1,4-dihydropyridine,
(k) 2,6-Dimethyl-3-(2-phthalimidocarbethoxy)-4-(2-chloro-6-nitrophenyl)-5-carbomethoxy-1,4-dihydropyridine,
(l) 2,6-Dimethyl-3-(2-phthalimidocarbethoxy)-4-(2-fluorophenyl)-5-carbomethoxy-1,4-dihydropyridine
(m) 2,6-dimethyl-3-(2-phthalimidocarbethoxy)-4-(3-fluorophenyl)-5-carbomethoxy-1,4-dihydropyridine,
(n) 2,6-Dimethyl-3-(2-phthalimidocarbethoxy)-4-(2-nitro-5-chlorophenyl)-5-carbomethoxy-1,4-dihydropyridine
(o) 2,6-Dimethyl-3-(2-phthalimidocarbethoxy)-4-(5-bromo-2-furyl)-5-carbomethoxy-1,4-dihydropyridine,
(p) 2,6-Dimethyl-3-(2-phthalimidocarbethoxy)-4-(2-furyl)-5-carbomethoxy-1,4-dihydropyridine,
(q) 2,6-Dimethyl-3-(2-phthalimidocarbethoxy)-4-(3-indolyl)-5-carbomethoxy-1,4-dihydropyridine,
(r) 2,6-Dimethyl-3-(2-phthalimidocarbethoxy)-4-(5-nitro-2-furyl)-5-carbomethoxy-1,4-dihydropyridine,
(s) 2,6-Dimethyl-3-(2-phthalimidocarbethoxy)-4-(2-pyridyl)-5-carbomethoxy-1,4-dihydropyridine,
(t) 2,6-Dimethyl-3-(2-phthalimidocarbethoxy)-4-(3-pyridyl)-5-carbomethoxy-1,4-dihydropyridine,
(u) 2,6-Dimethyl-3-(2-phthalimidocarbethoxy)-4-(2-thienyl)-5-carbomethoxy-1,4-dihydropyridine,
(v) 2,6-Dimethyl-3-(2-phthalimidocarbethoxy)-4-(3-thienyl)-5-carbomethoxy-1,4-dihydropyridine,
(w) 2,6-Dimethyl-3-(2-phthalimidocarbethoxy)-4-(3-quinolinyl)-5-carbomethoxy-1,4-dihydropyridine,
(x) 2,6-Dimethyl-3-(2-phthalimidocarbethoxy)-4-(2-pyrrolyl)-5-carbomethoxy-1,4-dihydropyridine and
(y) 2,6-Dimethyl-3-(2-phthalimidocarbethoxy)-4-(1-methyl-2-pyrrolyl)-5-carbomethoxy-1,4-dihydropyridine.

EXAMPLE 14

The general procedure of Examples 1C, 2, 3, 5C, 6C, 7C, 8E, 9C, 10B and 11C are individually repeated except that the methyl-3-aminocrotonate utilized therein is replaced by an equimolar amount of ethyl 3-amino-4,4,4-trifluorocrotonate and there is thereby produced
(a) 2-methyl-3-(2-phthalimidocarbethoxy)-4-(3-methylphenyl)-5-carbethoxy-6-trifluoromethyl-1,4-dihydropyridine,
(b) 2-methyl-3-(2-phthalimidocarbethoxy)-4-(3-nitrophenyl)-5-carbethoxy-6-trifluoromethyl-1,4-dihydropyridine,
(c) 2-methyl-3-(2-phthalimidocarbethoxy)-4-(3-trifluoromethylphenyl)-5-carbethoxy-6-trifluoromethyl-1,4-dihydropyridine,
(d) 2-methyl-3-(3-phthalimidocarbopropoxy)-4-(3-nitrophenyl)-5-carbethoxy-6-trifluoromethyl-1,4-dihydropyridine,
(e) 2-methyl-3-(6-phthalimidocarbohexoxy)-4-(3-nitrophenyl)-5-carbethoxy-6-trifluoromethyl-1,4-dihydropyridine,
(f) 2-methyl-3-(2-phthalimidinocarbethoxy)-4-(3-nitrophenyl)-5-carbethoxy-6-trifluoromethyl-1,4-dihydropyridine,
(g) 2-methyl-3-(2-isoindolinylcarbethoxy)-4-(3-nitrophenyl)-5-carbethoxy-6-trifluoromethyl-1,4-dihydropyridine,
(h) 2-methyl-3-(2-succinimidocarbethoxy)-4-(3-nitrophenyl)-5-carbethoxy-6-trifluoromethyl-1,4-dihydropyridine,
(i) 2-methyl-3-[2-(2-oxopyrrolidino)carbethoxy]-4-(3-nitrophenyl)-5-carbethoxy-6-trifluoromethyl-1,4-dihydropyridine, and
(j) 2-methyl-3-[2-(2,5-dimethylpyrrolyl)carbethoxy]-4-(3-nitrophenyl-5-carbethoxy-6-trifluoromethyl-1,4-dihydropyridine, respectively.

EXAMPLE 15

The general procedures of Examples 1C, 2, 3, 5C, 6C, 7C, 8E, 9C, 10B and 11C are repeated except that the methyl 3-aminocrotonate utilized therein is replaced by an equimolar amount of ethyl 3-amino-5-dimethylamino-2-pentenoate in each instance, and there is thereby produced:
(a) 2-methyl-3-(2-phthalimidocarbethoxy)-4-(3-methylphenyl)-5-carbethoxy-6-(2-dimethylaminoethyl)-1,4-dihydropyridine,
(b) 2-methyl-3-(2-phthalimidocarbethoxy)-4-(3-nitrophenyl)-5-carbethoxy-6-(2-dimethylaminoethyl)-1,4-dihydropyridine,
(c) 2-methyl-3-(2-phthalimidocarbethoxy)-4-(3-trifluoromethylphenyl)-5-carbethoxy-6-(2-dimethylaminoethyl)-1,4-dihydropyridine, (d) 2-methyl-3-(3-phthalimidocarbopropoxy)-4-(3-nitrophenyl)-5-carbethoxy-6-(2-dimethylaminoethyl)-1,4-dihydropyridine,
(e) 2-methyl-3-(6-phthalimidocarbohexoxy)-4-(3-nitrophenyl)-5-carbethoxy-6-(2-dimethylaminoethyl)-1,4-dihydropyridine,
(f) 2-methyl-3-(2-phthalimidinocarbethoxy)-4-(3-nitrophenyl)-5-carbethoxy-6-(2-dimethylaminoethyl)-1,4-dihydropyridine,
(g) 2-methyl-3-(2-isoindolinylcarbethoxy)-4-(3-nitrophenyl)-5-carbethoxy-6-(2-dimethylaminoethyl)-1,4-dihydropyridine,
(h) 2-methyl-3-(2-succinimidocarbethoxy)-4-(3-nitrophenyl)-5-carboethoxy-6-(2-dimethylaminoethyl)-1,4-dihydropyridine,
(i) 2-methyl-3-[2-(2-oxopyrrolidino)carbethoxy]-4-(3-nitrophenyl)-5-carbethoxy-6-(2-dimethylaminoethyl)-1,4-dihydropyridine,
(j) 2-methyl-3-[2-(2,5-dimethylpyrrolyl)carbethoxy]-4-(3-nitrophenyl)-5-carbethoxy-6-(2-dimethylaminoethyl)-1,4-dihydropyridine, respectively.

EXAMPLE 16

A. 2-phthalimidoethyl-4,4,4-trifluoroacetoacetate

The general procedure of Example 1B (procedure 1) is repeated except that the ethyl acetoacetate is replaced by an equimolar amount of 4,4,4-trifluoroacetaoacetate and there is thereby produced
(a) 2-phthalimidoethyl-4,4,4-trifluoroacetoacetate.

Similarly, the general procedures of Example 5B, 6B, 7B, 8D, 9B, 10A and 11B are each repeated as above except that the ethyl acetoacetate is replaced by an equimolar amount of 4,4,4-trifluoroacetoacetate and there are thereby produced.
(b) 3-phthalimidopropyl-4,4,4-trifluoroacetoacetate,
(c) 6-phthalimidohexyl-4,4,4-trifluroacetoacetate,
(d) N-2-phthalimidinoethyl-4,4,4-trifluroacetoacetate,
(e) 2-isoindolinylethyl-4,4,4-trifluroacetoacetate,
(f) 2-succinimidoethyl-4,4,4-trifluroacetoacetate,
(g) 2-(2-oxopyrrolidino)ethyl-4,4,4-trifluroacetoacetate, and
(h) 2-(2,5-dimethylpyrrolyl)ethyl-4,4,4-trifluroacetoacetate, respectively.

B. 2-trifluoromethyl-3-(2-phthalimidocarbethoxy)-4-(3-nitrophenyl)-5-carbomethoxy-6-methyl-1,4-dihydropyridine.

The general procedure of Example 2 is repeated except that the 2-phthalimidoethylacetoacetate utilized there is replaced by an equimolar amount of 2-phthalimidoethyl-4,4,4-trifluroacetoacetate, and there is thereby produced
(a) 2-trifluoromethyl-3-(2-phthalimidocarbethoxy)-4-(3-nitrophenyl)-5-carbomethoxy-6-methyl-1,4-dihydropyridine.

Similarly, utilizing the seven 4,4,4-trifluroacetoacetate, derivatives mentioned under Example 16A and repeating the general procedure of Example 2, there are produced
(b) 2-trifluoromethyl-3-(3-phthalimidocarbopropoxy)-4-(3-nitro-phenyl)-5-carbomethoxy-6-methyl-1,4-dihydropyridine,
(c) 2-trifluoromethyl-3-(6-phthalimidocarbohexoxy)-4-(3-nitrophenyl)-5-carbomethoxy-6-methyl-1,4-dihydropyridine,
(d) 2-trifluoromethyl-3-(2-phthalimidinocarbethoxy)-4-(3-nitrophenyl)-5-carbomethoxy-6-methyl-1,4-dihydropyridine,
(e) 2-trifluoromethyl-3-(2-isoindolinylcarbethoxy)-4-(3-nitrophenyl)-5-carbomethoxy-6-methyl-1,4-dihydropyridine,
(f) 2-trifluoromethyl-3-(2-succinimidocarbethoxy)-4-(3-nitrophenyl)-5-carbomethoxy-6-methyl-1,4-dihydropyridine,
(g) 2-trifluoromethyl-3-[2-(2-oxopyrrolidino)carbethoxy]-4-(3-nitrophenyl)-5-carbomethoxy-6-methyl-1,4-dihydropyridine, and
(h) 2-trifluoromethyl-3-[2-(2,5-dimethylpyrrolyl)carbethoxy]-4-(3-nitrophenyl)-5-carbomethoxy-6-methyl-1,4-dihydropyridine, respectively.

EXAMPLE 17

The general procedure of Example 2 is repeated except that methyl-3-aminocrotonate and 2-phthalimidoethyl acetoacetate are replaced by equimolar amounts of Ethyl 3-amino-4,4,4-trifluorocrotonate and 2-phthalimidoethyl-4,4,4-trifluoroacetoacetate, and there is thereby produced
(a) 2,6-di-trifluoromethyl-3-(2-phthalimidocarbethoxy)-4-(3-nitrophenyl)-5-carbethoxy-1,4-dihydropyridine.

Similarly, utilizing equimolar amounts of the seven 4,4,4-trifluoroacetoacetate derivatives mentioned under Example 16A in place of 2-phthalimidoethyl-4,4,4-trifluoroacetoacetate, there are thereby produced, respectively:
(b) 2,6-di-trifluoromethyl-3-(2-phthalimidocarbopropoxy)-4-(3-nitrophenyl)-5-carbethoxy-1,4-dihydropyridine,
(c) 2,6-di-trifluoromethyl-3-(2-phthalimidocabohexoxy)-4-(3-nitrophenyl)-5-carbethoxy-1,4-dihydropyridine,
(d) 2,6-di-trifluoromethyl-3-(2-phthalimidinocarbethoxy)-4-(3-nitrophenyl)-5-carbethoxy-1,4-dihydropyridine,
(e) 2,6-di-trifluoromethyl-3-(2-isoindolinylcarbethoxy)-4-(3-nitrophenyl)-5-carbethoxy-1,4-dihydropyridine,
(f) 2,6-di-trifluoromethyl-3-(2-succinimidocarbethoxy)-4-(3-nitrophenyl)-5-carbethoxy-1,4-dihydropyridine,
(g) 2,6-di-trifluoromethyl-3-[2-(2-oxopyrrolidino)carbethoxy]-4-(3-nitrophenyl)-5-carbethoxy-1,4-dihydropyridine, and
(h) 2,6-di-trifluoromethyl-3-[2-(2,5-dimethylpyrrolyl)carb-ethoxy]-4-(3-nitrophenyl)-5-carbethoxy-1,4-dihydropyridine.

EXAMPLE 18

The general procedure of Example 4 is repeated except that the 2-phthalimidoethyl acetoacetate is replaced by an equimolar amount of 2-phthalimidoethyl-4,4,4-trifluoroacetoacetate and there is thereby produced
(a) 2,6-di-trifluoromethyl-3,5-di-(2-phthalimidocarbethoxy)-4-(3-nitrophenyl)-1,4-dihydropyridine.

Similarly, utilizing equimolar amounts of the seven 4,4,4-trifluoroacetoacetate derivatives mentioned under Example 16A in place of 2-phthalimidoethyl-4,4,4-trifluoroacetoacetate are thereby produced, respectively.
(b) 2,6-di-trifluoromethyl-3,5-di-(2-phthalimidocarbopropoxy)-4-(3-nitrophenyl)1,4-dihydropyridine,
(c) 2,6-di-trifluoromethyl-3,5-di-(2-phthalimidocarbohexoxy)-4-(3-nitrophenyl)-1,4-dihydropyridine,
(d) 2,6-di-trifluoromethyl-3,5-di-(2-phthalimidinocarbethoxy)-4-(3-nitrophenyl)-1,4-dihydropyridine,
(e) 2,6-di-trifluoromethyl-3,5-di-(2-isoindolinylcarbethoxy)-4-(3-nitrophenyl)-1,4-dihydropyridine, (f) 2,6-di-trifluoromethyl-3,5-di-(2-succinimidocarbethoxy)-4-(3-nitrophenyl)-1,4-dihydropyridine,
(g) 2,6-di-trifluoromethyl-3,5-di-[2-(2-oxopyrrolidino)-carbethoxy]-4-(3-nitrophenyl)-1,4-dihydropyridine, and
(h) 2,6-di-trifluoromethyl-3,5-di-[(2,5-dimethylpyrrolyl)carbethoxy]-4-(3-nitrophenyl)-1,4-dihydropyridine.

EXAMPLE 19

The general procedure of Example 7C is repeated, except that the 3-nitrobenzaldehyde utilized therein is replaced, successively, with an equimolar amount of each of the 25 aldehydes listed in Example 13 to produce, respectively:

(a) 2,6-Dimethyl-3-(2-phthalimidinocarbethoxy)-4-(2-nitrophenyl)-5-carbomethoxy-1,4-dihydropyridine,
(b) 2,6-Dimethyl-3-(2-phthalimidinocarbethoxy)-4-(2-chlorophenyl)-5-carbomethoxy-1,4-dihydropyridine,
(c) 2,6-Dimethyl-3-(2-phthalimidinocarbethoxy)-4-(3-chlorophenyl)-5-carbomethoxy-1,4-dihydropyridine,
(d) 2,6-Dimethyl-3-(2-phthalimidinocarbethoxy)-4-(3-cyanophenyl)-5-carbomethoxy-1,4-dihydropyridine,
(e) 2,6-Dimethyl-3-(2-phthalimidinocarbethoxy)-4-(3-methoxy-phenyl)-5-carbomethoxy-1,4-dihydropyridine,
(f) 2,6-Dimethyl-3-(2-phthalimidinocarbethoxy)-4-(2-bromophenyl)-5-carbomethoxy-1,4-dihydropyridine,
(g) 2,6-Dimethyl-3-(2-phthalimidinocarbethoxy)-4-(2-chloro-6-fluorophenyl)-5-carbomethoxy-1,4-dihydropyridine,
(h) 2,6-Dimethyl-3-(2-phthalimidinocarbethoxy)-4-(2-chloro-5-nitrophenyl)-5-carbomethoxy-1,4-dihydropyridine,
(i) 2,6-Dimethyl-3-(2-phthalimidinocarbethoxy)-4-(3-bromophenyl)-5-carbomethoxy-1,4-dihydropyridine,
(j) 2,6-Dimethyl-3-(2-phthalimidinocarbethoxy)-4-(2,6-dinitrophenyl)-5-carbomethoxy-1,4-dihydropyridine,
(k) 2,6-Dimethyl-3-(2-phthalimidinocarbethoxy)-4-(2-chloro-6-nitrophenyl)-5-carbomethoxy-1,4-dihydropyridine,
(l) 2,6-Dimethyl-3-(2-phthalimidinocarbethoxy)-4-(2-fluorophenyl)-5-carbomethoxy-1,4-dihydropyridine,
(m) 2,6-Dimethyl-3-(2-phthalimidinocarbethoxy)-4-(3-fluorophenyl)-5-carbomethoxy-1,4-dihydropyridine,
(n) 2,6-Dimethyl-3-(2-phthalimidinocarbethoxy)-4-(2-nitro-5-chlorophenyl)-5-carbomethoxy-1,4-dihydropyridine
(o) 2,6-Dimethyl-3-(2-phthalimidinocarbethoxy)-4-(5-bromo-2-furyl)-5-carbomethoxy-1,4-dihydropyridine,
(p) 2,6-Dimethyl-3-(2-phthalimidinocarbethoxy)-4-(2-furyl)-5-carbomethoxy-1,4-dihydropyridine,
(q) 2,6-Dimethyl-3-(2-phthalimidinocarbethoxy)-4-(3-indolyl)-5-carbomethoxy-1,4-dihydropyridine,
(r) 2,6-Dimethyl-3-(2-phthalimidinocarbethoxy)-4-(5-nitro-2-furyl)-5-carbomethoxy-1,4-dihydropyridine,
(s) 2,6-Dimethyl-3-(2-phthalimidinocarbethoxy)-4-(2-pyridyl)-5-carbomethoxy-1,4-dihydropyridine,
(t) 2,6-Dimethyl-3-(2-phthalimidinocarbethoxy)-4-(3-pyridyl)-5-carbomethoxy-1,4-dihydropyridine,
(u) 2,6-Dimethyl-3-(2-phthalimidinocarbethoxy)-4-(2-thienyl)-5-carbomethoxy-1,4-dihydropyridine,
(v) 2,6-Dimethyl-3-(2-phthalimidinocarbethoxy)-4-(3-thienyl)-5-carbomethoxy-1,4-dihydropyridine,
(w) 2,6-dimethyl-3-(2-phthalimidinocarbethoxy)-4-(3-quinolinyl)-5-carbomethoxy-1,4-dihydropyridine,
(x) 2,6-Dimethyl-3-(2-phthalimidinocarbethoxy)-4-(2-pyrrolyl)-5-carbomethoxy-1,4-dihydropyridine and
(y) 2,6-Dimethyl-3-(2-phthalimidinocarbethoxy)-4-(1-methyl-2-pyrrolyl)-5-carbomethoxy-1,4-dihydropyridine.

EXAMPLE 20

The general procedure of Example 8E is repeated, except that the 3-nitrobenzaldehyde used therein is replaced, successively, with an equimolar amount of each of the 25 aldehydes listed in Example 13 to produce, respectively:

(a) 2,6-Dimethyl-3-(2-isoindolinylcarbethoxy)-4(2-nitrophenyl)-5-carbomethoxy-1,4-dihydropyridine,
(b) 2,6-Dimethyl-3-(2-isoindolinylcarbethoxy)-4-(2-chlorophenyl)-5-carbomethoxy-1,4-dihydropyridine,
(c) 2,6-Dimethyl-3-(2-isoindolinylcarbethoxy)-4-(3-chlorophenyl)-5-carbomethoxy-1,4-dihydropyridine,
(d) 2,6-Dimethyl-3-(2-isoindolinylcarbethoxy)-4-(3-cyanophenyl)-5-carbomethoxy-1,4-dihydropyridine,
(e) 2,6-Dimethyl-3-(2-isoindolinylcarbethoxy)-4-(3-methoxy-phenyl)-5-carbomethoxy-1,4-dihydropyridine,
(f) 2,6-Dimethyl-3-(2-isoindolinylcarbethoxy)-4-(2-bromophenyl)-5-carbomethoxy-1,4-dihydropyridine,
(g) 2,6-Dimethyl-3-(2-isoindolinylcarbethoxy)-4-(2-chloro-6-fluorophenyl)-5-carbomethoxy-1,4-dihydropyridine,
(h) 2,6-Dimethyl-3-(2-isoindolinylcarbethoxy)-4-(2-chloro-5-nitrophenyl)-5-carbomethoxy-1,4-dihydropyridine,
(i) 2,6-Dimethyl-3-(2-isoindolinylcarbethoxy)-4-(3-bromophenyl)-5-carbomethoxy-1,4-dihydropyridine,
(j) 2,6-Dimethyl-3-(2-isoindolinylcarbethoxy)-4-(2,6-dinitrophenyl)-5-carbomethoxy-1,4-dihydropyridine,
(k) 2,6-Dimethyl-3-(2-isoindolinylcarbethoxy)-4-(2-chloro-6-nitrophenyl)-5-carbomethoxy-1,4-dihydropyridine,
(l) 2,6-Dimethyl-3-(2-isoindolinylcarbethoxy)-4-(2-fluorophenyl)-5-carbomethoxy-1,4-dihydropyridine
(m) 2,6-Dimethyl-3-(2-isoindolinylcarbethoxy)-4-(3-fluorophenyl)-5-carbomethoxy-1,4-dihydropyridine,
(n) 2,6-Dimethyl-3-(2-isoindolinylcarbethoxy)-4-(2-nitro-5-chlorophenyl)-5-carbomethoxy-1,4-dihydropyridine
(o) 2,6-Dimethyl-3-(2-isoindolinylcarbethoxy)-4-(5-bromo-2-furyl)-5-carbomethoxy-1,4-dihydropyridine,
(p) 2,6-Dimethyl-3-(2-isoindolinylcarbethoxy)-4-(2-furyl)-5-carbomethoxy-1,4-dihydropyridine,
(q) 2,6-Dimethyl-3-(2-isoindolinylcarbethoxy)-4-(3-indolyl)-5-carbomethoxy-1,4-dihydropyridine,
(r) 2,6-Dimethyl-3-(2-isoindolinylcarbethoxy)-4-(5-nitro-2-furyl)-5-carbomethoxy-1,4-dihydropyridine,
(s) 2,6-Dimethyl-3-(2-isoindolinylcarbethoxy)-4-(2-pyridyl)-5-carbomethoxy-1,4-dihydropyridine,
(t) 2,6-Dimethyl-3-(2-isoindolinylcarbethoxy)-4-(3-pyridyl)-5-carbomethoxy-1,4-dihydropyridine,
(u) 2,6-Dimethyl-3-(2-isodinolinylcarbethoxy)-4-(2-thienyl)-5-carbomethoxy-1,4-dihydropyridine,
(v) 2,6-Dimethyl-3-(2-isoindolinylcarbethoxy)-4-(3-thienyl)-5-carbomethoxy-1,4-dihydropyridine,
(w) 2,6-dimethyl-3-(2-isoindolinylcarbethoxy)-4-(3-quinolinyl)-5-carbomethoxy-1,4-dihydropyridine,
(x) 2,6-Dimethyl-3-(2-isoindolinylcarbethoxy)-4-(2-pyrrolyl)-5-carbomethoxy-1,4-dihydropyridine and (y) 2,6-Dimethyl-3-(2-isoindolinylcarbethoxy)-4-(1-methyl-2-pyrrolyl)-5-carbomethoxy-1,4-dihydropyridine.

EXAMPLE 21

The general procedure of Example 11C is repeated, except that the 3-nitrobenzaldehyde used therein is replaced, successively, with an equimolar amount of each of the 25 aldehydes listed in Example 13 to produce, respectively:

(a) 2,6-Dimethyl-3-[2-(2,5-dimethylpyrrolyl)carbethoxy]-4-(2-nitrophenyl)-5-carbomethoxy-1,4-dihydropyridine, (b) 2,6-Dimethyl-3-[2-(2,5-dimethylpyrrolyl)carbethoxy]-4-(2-chlorophenyl)-5-carbomethoxy-1,4-dihydropyridine, (c) 2,6-Dimethyl-3-[2-(2,5-dimethylpyrrolyl)carbethoxy]-4-(3-chlorophenyl)-5-carbomethoxy-1,4-dihydropyridine, (d) 2,6-Dimethyl-3-[2-(2,5-dimethylpyrrolyl)carbethoxy]-4-(3-cyanophenyl)-5-carbomethoxy-1,4-dihydropyridine, (e) 2,6-Dimethyl-3-[2-(2,5-dimethylpyrrolyl)carbethoxy]-4-(3-methoxy-phenyl)-5-carbomethoxy-1,4-dihydropyridine, (f) 2,6-Dimethyl-3-[2-(2,5-dimethylpyrrolyl)carbethoxy]-4-(2-bromophenyl)-5-carbomethoxy-1,4-dihydropyridine, (g) 2,6-Dimethyl-3-[2-(2,5-dimethylpyrrolyl)carbethoxy]-4-(2-chloro-6-fluorophenyl)-5-carbomethoxy-1,4-dihydropyridine, (h) 2,6-Dimethyl-3-[2-(2,5-dimethylpyrrolyl)carbethoxy]-4-(2-chloro-5-nitrophenyl)-5-carbomethoxy-1,4-dihydropyridine, (i) 2,6-Dimethyl-3-[2-(2,5-dimethylpyrrolyl)carbethoxy]-4-(3-bromophenyl)-5-carbomethoxy-1,4-dihydropyridine, (j) 2,6-Dimethyl-3-[2-(2,5-dimethylpyrrolyl)carbethoxy]-4-(2,6-dinitrophenyl)-5-carbomethoxy-1,4-dihydropyridine, (k) 2,6-Dimethyl-3-[2-(2,5-dimethylpyrrolyl)carbethoxy]-4-(2-chloro-6-nitrophenyl)-5-carbomethoxy-1,4-dihydropyridine, (l) 2,6-Dimethyl-3-[2-(2,5-dimethylpyrrolyl)carbethoxy]-4-(2-fluorophenyl)-5-carbomethoxy-1,4-dihydropyridine (m) 2,6-Dimethyl-3-[2-(2,5-dimethylpyrrolyl)carbethoxy]-4-(3-fluorophenyl)-5-carbomethoxy-1,4-dihydropyridine, (n) 2,6-Dimethyl-3-[2-(2,5-dimethylpyrrolyl)carbethoxy]-4-(2-nitro-5-chlorophenyl)-5-carbomethoxy-1,4-dihydropyridine (o) 2,6-Dimethyl-3-[2-(2,5-dimethylpyrrolyl)carbethoxy]-4-(5-bromo-2-furyl)-5-carbomethoxy-1,4-dihydropyridine, (p) 2,6-Dimethyl-3-[2-(2,5-dimethylpyrrolyl)carbethoxy]-4-(2-furyl)-5-carbomethoxy-1,4-dihydropyridine, (q) 2,6-Dimethyl-3-[2-(2,5-dimethylpyrrolyl)carbethoxy]-4-(3-indolyl)-5-carbomethoxy-1,4-dihydropyridine, (r) 2,6-Dimethyl-3-[2-(2,5-dimethylpyrrolyl)carbethoxy]-4-(5-nitro-2-furyl)-5-carbomethoxy-1,4-dihydropyridine, (s) 2,6-Dimethyl-3-[2-(2,5-dimethylpyrrolyl)carbethoxy]-4-(2-pyridyl)-5-carbomethoxy-1,4-dihydropyridine, (t) 2,6-Dimethyl-3-[2-(2,5-dimethylpyrrolyl)carbethoxy]-4-(3-pyridyl)-5-carbomethoxy-1,4-dihydropyridine, (u) 2,6-Dimethyl-3-[2-(2,5-dimethylpyrrolyl)carbethoxy]-4-(2-thienyl)-5-carbomethoxy-1,4-dihydropyridine, (v) 2,6-Dimethyl-3-[2-(2,5-dimethylpyrrolyl)carbethoxy]-4-(3-thienyl)-5-carbomethoxy-1,4-dihydropyridine, (w) 2,6-Dimethyl-3-[2-(2,5-dimethylpyrrolyl)carbethoxy]-4-(3-quinolinyl)-5-carbomethoxy-1,4-dihydropyridine, (x) 2,6-Dimethyl-3-[2-(2,5-dimethylpyrrolyl)carbethoxy]-4-(2-pyrrolyl)-5-carbomethoxy-1,4-dihydropyridine and (y) 2,6-Dimethyl-3-[2-(2,5-dimethylpyrrolyl)carbethoxy]-4-(1-methyl-2-pyrrolyl)-5-carbomethoxy-1,4-dihydropyridine.

PHARMACOLOGY

A. Binding Assay for Drugs Acting at the DHP Site of the Calcuim Channel.

The assay was carried out as described by Fairhurst et al., Life Sciences, 32, 1331 (1983). Washed rabbit skeletal muscle membranes (fraction 2-8X) were incubated for 30 minutes at 25° C. in 2 ml final volume of medium containing 12.5 mM HEPES buffer pH 7.4 and $0.5 \times 10^{-9}$M $^3$H-nitrendipine having a specific activity of approximately 17 Ci/m mol.

Parallel experiments contained, additionally, unlabelled nifedipine at a final concentration of $10^{-6}$M, to give the non-specific binding values.

The incubation tubes were rapidly chilled in ice and the contents filtered through Whatman GF/B filters on a Millipore manifold, and the filters washed with $2 \times 10$ ml ice-cold HEPES buffer. The filters were placed in scintillation counting vials with 8 ml of Cytoscint cocktail, disrupted mechanically by shaking for 30 minutes and counted.

Specific binding was determined by subtracting the radioactivity in the presence of nifedipine from that in the absence. Drugs which interact at the DHP site will reduce this specific binding in a dose-dependent manner. The assays for the compounds of this invention were made with logarithmically spaced concentrations, the data were plotted on a probit-concentration plot, and the $IC_{50}$ read off. The $K_I$ of the drug was calculated by standard techniques. The results of the assay are shown in Table I.

TABLE I*

| Ex. No. | $R_3$ | —A—$R_4$ | $R_6$ | $K_I$(moles) |
|---|---|---|---|---|
| 1. | $CH_3$ | —(CH$_2$)$_2$—N(phthalimido) | 3-methylphenyl | $1.97 \times 10^{-8}$ |

TABLE I*-continued

| Ex. No. | $R_3$ | $-A-R_4$ | $R_6$ | $K_I$(moles) |
|---|---|---|---|---|
| 2. | $CH_3$ | $-(CH_2)_2-$phthalimide | 3-$NO_2$-phenyl | $7 \times 10^{-10}$ |
| 3. | $CH_3$ | $-(CH_2)_2-$phthalimide | 3-$CF_3$-phenyl | $4.8 \times 10^{-8}$ |
| 4. | $-(CH_2)_2-$phthalimide | $-(CH_2)_2-$phthalimide | 3-$NO_2$-phenyl | $2.5 \times 10^{-9}$ |
| 5. | $CH_3$ | $-(CH_2)_3-$phthalimide | 3-$NO_2$-phenyl | $4.8 \times 10^{-9}$ |
| 6. | $CH_3$ | $-(CH_2)_6-$phthalimide | 3-$NO_2$-phenyl | $1.9 \times 10^{-9}$ |
| 7. | $CH_3$ | $-(CH_2)_2-$(2-oxo-isoindolin-1-yl) | 3-$NO_2$-phenyl | $2 \times 10^{-8}$ |
| 8. | $CH_3$ | $-(CH_2)_2-$isoindolinyl | 3-$NO_2$-phenyl | $3.5 \times 10^{-9}$ |
| 9. | $CH_3$ | $-(CH_2)_2-$succinimide | 3-$NO_2$-phenyl | $1.5 \times 10^{-7}$ |
| 10. | $CH_3$ | $-(CH_2)_2-$(2-oxopyrrolidin-1-yl) | 3-$NO_2$-phenyl | $2.7 \times 10^{-7}$ |

TABLE I*-continued

| Ex. No. | R₃ | —A—R₄ | R₆ | $K_I$(moles) |
|---|---|---|---|---|
| 11. | CH₃ | CH₃—CH=CH—CH₂— (dimethyl diene) | 3-NO₂-C₆H₄— | $2.5 \times 10^{-9}$ |
| 12. | —(CH₂)₂—N(2,5-dimethylpyrrolyl) | —(CH₂)₂—N(2,5-dimethylpyrrolyl) | 3-NO₂-C₆H₄— | $2.5 \times 10^{-9}$ |
| Nifedipine | CH₃ | CH₃ | 3-NO₂-C₆H₄— | $7.6 \times 10^{-9}$ |
| Nicardipine | CH₃ | —(CH₂)₂—N(CH₃)(CH₂C₆H₅) | 3-NO₂-C₆H₄— | $1.1 \times 10^{-9}$ |

*For examples given, $R_1 = R_2 = CH_3$

B. Hypotensive Activity:

Systolic arterial blood pressure was measured with the indirect tail cuff method in spontaneous hypertensive rates (SHR). The change in baseline pressure (170–210 mm Hg) was recorded at various time points following oral administration of 10 m mol/Kg of the test compound in polyethylene glycol. The results are given in Table II.

TABLE II

| | | Hypotensive Effect (Oral Administration) | | | | | |
|---|---|---|---|---|---|---|---|
| | | Mean Change in Blood Pressure (Pressure before Administration minus pressure after Administration mm Hg) | | | | | |
| Test Compound | No. of Animals | 10 min | 20 min | 30 min | 60 min | 90 min | 120 min |
| Compound of Ex. 1 | 3 | 17 | 10 | 4 | −2 | 5 | −4 |
| Compound of Ex. 2 | 2 | 9 | 10 | 10 | 6 | 0 | 0 |
| Compound of Ex. 4 | 3 | 9 | 8 | 14 | 11 | 14 | 10 |
| Compound of Ex. 5 | 2 | −5 | −14 | −10 | −6 | −6 | −5 |
| Compound of Ex. 6 | 2 | 18 | 10 | 12 | 14 | 2 | 0 |
| Compound of Ex. 7 | 2 | 14 | 19 | 10 | 10 | 20 | 19 |
| Compound of Ex. 8 | 3 | 36 | 30 | 32 | 16 | 4 | 2 |
| Compound of Ex. 9 | 3 | 36 | 10 | 5 | 3 | 19 | 11 |
| Compound of Ex. 10 | 2 | −17 | −5 | 11 | 7 | 6 | 7 |
| Compound of Ex. 11 | 3 | 36 | 40 | 39 | 29 | 29 | 20 |
| Nifedipine | 6 | 37 | 36 | 20 | 15 | 4 | 4 |

What is claimed is:

1. A compound of the formula:

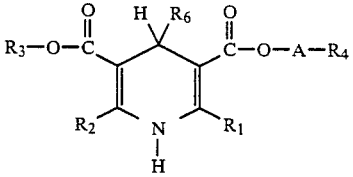

wherein $R_1$ and $R_2$ are each independently: amino, trifluoromethyl, pentafluoroethyl, lower alkoxy, lower akenyl, or lower alkynyl or branched or unbranched lower alkyl, which is unsubstituted or is substituted with cyano, hydroxy, lower alkanoy loxy, hydrazino, lower alkyl amino, or di-(lower alkyl)-amino or 5- or 6-membered saturated nitrogen-containing heterocylic-1-yl selected from the group consisting of pyrrolidinyl, piperazinyl, piperazinyl, piperidinyl, 1-methyl-4-piperazinyl and morpholinyl, which is unsubstituted or is substituted with oxo, hydroxy, (lower) alkyl, or hydroxy (lower alkyl);

$R_3$ is straight- or branched-chain $C_1$ to $C_{12}$ alkyl, lower alkenyl, lower alkynyl, or cycloalkyl, and is either unsubstituted or substituted with hydroxy, lower alkanoy loxy, cyano, di(lower alkyl) amino, 5 or 6 membered saturated nitrogen-containing heterocyclic-1-yl, selected from the group consisting of pyrrolidinyl, piperazinyl, piperidinyl, 1-methyl-4-piperazinyl and morpholinyl, or $R_3$ is —A—R₄;

A is a straight- or branched-chain hydrocarbon moiety containing from 2 to 12 carbon atoms and from 0 to 2 double bonds;

R₄ is selected from the group consisting of:

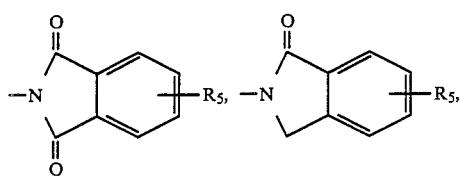, 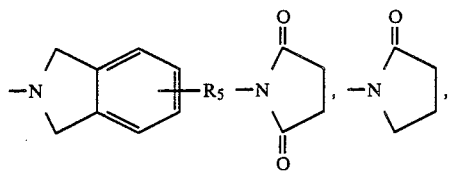

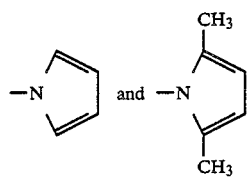

$R_5$ is hydrogen, nitro, cyano, azido, amino, trifluoromethyl, lower alkylamino, diloweralkylamino, halo, carboxyl, lower alkoxy carbonyl, lower alkyl, lower alkenyl, lower alkynyl, cycloalkyl, lower alkanoylamino, carboxamido, sulfonamido, and $SO_m$-(lower) alkyl where m is 0, 1 or 2 and $R_6$ is quinolyl and is either unsubstituted or is substituted with from 1 to 3 identical or different substituents selected from the group consisting of phenyl, lower alkyl, lower alkenyl, lower alkynyl, lower alkoxy, lower alkenoxy, lower alkynoxy, dioxyloweralkylene, halogen, trifluoromethyl, hydroxyl, amino, lower alkylamino, lower 2 dialkylamino, nitro, cyano, azido, carboxy, lower alkoxy carbonyl, carboxamido, sulphonamido, $SO_m$-loweralkyl, and $SO_m$-trifluoro (lower alkyl), wherein m is 0, 1 or 2 and wherein the lower alkyl and lower alkoxy substituents are unsubstituted or are in turn substituted with lower alkoxy, halogen, carboxyl, lower alkoxy carbonyl, amino, lower alkylamino or lower dialkylamino, or a pharmaceutically-acceptable salt thereof.

2. The compound of claim 1, in which $R_1$ and $R_2$ are individually methyl, ethyl, n-propyl, isopropyl, n-butyl, isobutyl, t-butyl, allyl, propargyl, amino, cyanomethyl, trifluoromethyl, (lower alkyl)amino(lower alkyl), or di(lower alkyl)amino(lower alkyl).

3. The compound of claim 1, in which one of $R_1$ and $R_2$ is methyl.

4. The compound of claim 1, in which $R_1$ is methyl.

5. The compound of claim 1, in which one of $R_1$ and $R_2$ is trifluoromethyl.

6. The compound of claim 1, in which $R_3$ is lower alkyl.

7. The compound of claim 1, in which $R_3$ is —A—$R_4$.

8. The compound of claim 1, in which $R_4$ is

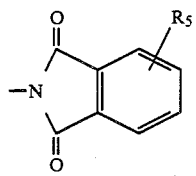

9. The compound of claim 1, in which $R_4$ is

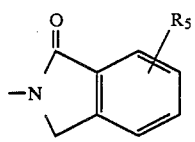

10. The compound of claim 1, in which $R_4$ is

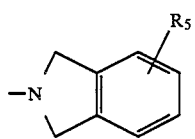

11. The compound of claim 1, in which $R_4$ is

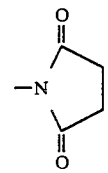

12. The compound of claim 1, in which $R_4$ is

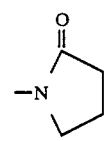

13. The compound of claim 1, in which $R_4$ is

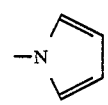

14. The compound of claim 1, in which $R_4$ is

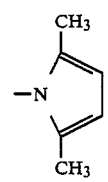

15. A pharmaceutical composition, comprising a pharmacologically-effective calcium channel antagonistic amount of the compound of claim 1, in combination with a pharmaceutically-acceptable carrier or excipient.

16. A method for treating coronary insufficiency, hypertension, angina pectoris, cardiac arrythmia, heart attack, or coronary vasospasm, comprising the step of administering an effective amount of a compound of claim 1.

17. A method of medical treatment, comprising administering to a mammal an effective amount of a compound of claim 1 to effect calcium channel antagonist activity.

* * * * *